(12) United States Patent
Williams

(10) Patent No.: US 7,196,053 B2
(45) Date of Patent: Mar. 27, 2007

(54) ODORANT COMPOUNDS

(75) Inventor: Alvin Scott Williams, Nyon (CH)

(73) Assignee: Firmenich SA, Geneva (CH)

( * ) Notice: Subject to any disclaimer, the term of this patent is extended or adjusted under 35 U.S.C. 154(b) by 325 days.

(21) Appl. No.: 10/792,375

(22) Filed: Mar. 2, 2004

(65) Prior Publication Data
US 2004/0186043 A1    Sep. 23, 2004

(30) Foreign Application Priority Data
Mar. 19, 2003 (WO) .................. PCT/IB03/01079

(51) Int. Cl.
A61K 8/18 (2006.01)
(52) U.S. Cl. ................. 512/25; 512/8; 512/22; 512/26; 512/27; 560/231; 560/249
(58) Field of Classification Search .......... 512/8, 512/22, 26, 27, 25; 560/231, 249
See application file for complete search history.

(56) References Cited
U.S. PATENT DOCUMENTS
5,166,412 A * 11/1992 Giersch et al. ............ 560/231

FOREIGN PATENT DOCUMENTS
EP    0 472 966    9/1994
EP    1 262 474    12/2002

* cited by examiner

Primary Examiner—Monique T. Cole
(74) Attorney, Agent, or Firm—Winston & Strawn LLP

(57) ABSTRACT

The present invention relates to the field of perfumery, and more precisely to a compound of formula (I)

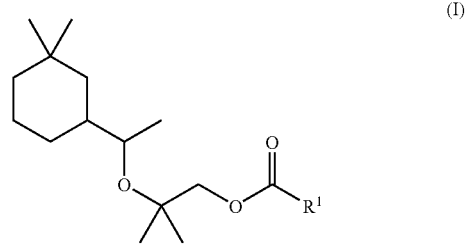

(I)

wherein $R^1$ represents an $C_2$ to $C_4$ unsaturated hydrocarbon radical.

The present invention concerns also the use of said compound in the perfumery industry as well as the compositions or articles associated with said compound.

12 Claims, No Drawings

ODORANT COMPOUNDS

TECHNICAL FIELD

The present invention relates to the field of perfumery. More particularly, it concerns an ester of the 2-[1-(3',3'-dimethyl-1'-cyclohexyl)ethoxy]-2-methylpropanol and of a $C_3$ to $C_5$ alkenoate.

BACKGROUND ART

To the best of our knowledge only one compound of formula (I), as defined below, has been reported in the prior art, namely 2-[1-(3,3-dimethylcyclohexyl)ethoxy]-2-methylpropyl 2-methyl-2-butenoate. Said compound has been reported in EP 1262474 as chemical intermediate for the synthesis of a cyclopropyl derivative.

In the patent EP 472966 there are reported compounds which are useful perfuming ingredients but differ from those of the present invention by the fact that they are saturated esters.

In the prior art mentioned above there is no mention, nor suggestion, of the olfactive properties of the compounds of the present invention.

SUMMARY OF THE INVENTION

A first object of the present invention is a compound of formula

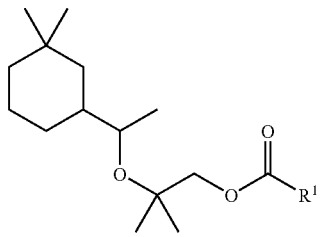

(I)

in the form of anyone of its isomers or a mixture thereof, and in which $R^1$ represents a linear or branched $C_2$ to $C_4$ alkenyl group.

Further objects of the present invention are the use in perfumery of said compound and the compositions or the articles comprising as active ingredient at least a compound of formula (I).

DETAILED DESCRIPTION OF THE PREFERRED EMBODIMENTS

Surprisingly, we have now established that a compound of formula

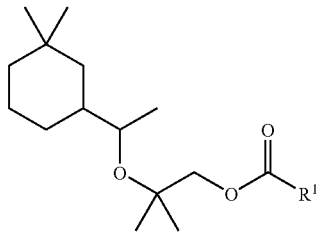

(I)

in the form of anyone of its isomers or a mixture thereof, and in which $R^1$ represents a linear or branched $C_2$ to $C_4$ alkenyl group;

possesses surprising odor properties, of the musky and green type, which have been found to be particularly useful and appreciated for the preparation of perfumes, perfuming compositions and perfumed products.

According to a particular embodiment of the invention, a compound of formula:

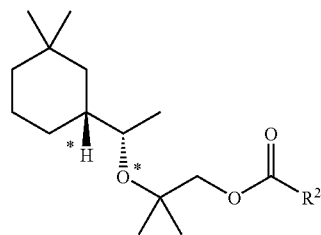

(II)

in the form of any of its isomers or a mixture thereof, and in which $R^2$ represents a linear or branched $C_2$ or $C_3$ 1-alkenyl group, and the hydrogen and oxygen atom marked with an asterisk are in a trans configuration, is preferred.

In particular, (1S,1'R)-2-[1-(3',3'-dimethyl-1'-cyclohexyl)ethoxy]-2-methylpropyl 2-propenoate possesses a powerful and persistent musky and green odor which is very original. More precisely the odor of said compound possesses at the same time a musky-ambrette and a fresh green character, together with a Galbanum and green pear undernote.

To the best of our knowledge, the combination of a musky and green character in the odor of a single compound has never been reported in the prior art. Moreover, the odor of said compounds has been found to be also very diffusive, a property which is quite rare for a compound possessing a musky note.

Another example of invention's compound is (1S,1'R)-2-[1-(3',3'-dimethyl-1'-cyclohexyl)ethoxy]-2-methylpropyl (E)-2-butenoate which possesses a similar but weaker note that its lower analogue above mentioned, i.e. the 2-propenoate.

The propenoate derivative is a preferred compound of the invention.

Moreover, due to the surprising properties of the compounds of formula (I), another object of the present invention is a perfuming composition comprising:

i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. As solid carrier one may cite, as non-limiting examples, absorbing gums or polymers, or yet an encapsulating materials. The encapsulation is a well known process to a person skilled in the art, and may be performed, for instance, using techniques such as spraydrying, agglomeration or yet extrusion; or consists of a coating encapsulation, including coacervation and complex coacervation techniques.

Generally speaking, by "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart an hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Generally speaking, by "perfumery adjuvant" we mean here an ingredient capable of imparting additional added benefit such as a color, a particular light resistance, chemical stability and etceteras. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particularly useful embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Its is also understood here that, unless otherwise indicated or described, any mixture resulting directly from a chemical synthesis, e.g. without an adequate purification, in which the compound of the invention would be involved as a starting, intermediate or end-product could not be considered as a perfuming composition according to the invention.

Furthermore, the invention compound can also be advantageously used in all the fields of modern perfumery to positively impart or modify the odor of a consumer product into which said compound (I) is added. Consequently, a perfumed article comprising:

i) as perfuming ingredient, at least one compound of formula (I) or an invention's perfuming composition; and
ii) a consumer product base is also an object of the present invention.

For the sake of clarity, it has to be mentioned that, by "consumer product base" we mean here a consumer product which can be associated with a perfuming composition, i.e. a consumable product such as a detergent or a perfume. In other words, a perfumed article according to the invention comprises the functional formulation, as well as optionally additional benefit agents, corresponding to a desired consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer products include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention compound, so that it may be necessary to protect the latter from premature decomposition, for example by encapsulation.

The proportions in which a compound of formula (I) can be incorporated into the various aforementioned articles or compositions vary within a wide range of values. These values are dependent on the nature of the article or product to be perfumed and on the olfactory effect desired as well as on the nature of the co-ingredients in a given composition when the compounds according to the invention are mixed with perfuming co-ingredients, solvents or additives commonly used in the art.

For example, in the case of perfuming compositions, typical concentrations are in the order of 1% to 20% by weight, or even more, of the compounds of the invention based on the weight of the composition into which they are incorporated. Concentrations lower than these, such as in the order of 0.05% to 1% by weight, can be used when these compounds are incorporated into perfumed articles.

As mentioned above, the invention concerns the use of a compound of formula (I) as perfuming ingredients. In other words it concerns a method to confer, enhance, improve or modify the odor properties of a perfuming composition or of a perfumed article, which method comprise adding to said composition or article an effective amount of at least a compound of formula (I). By "use of a compound of formula (I)" it has to be understood here also the use of an invention's composition.

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 MHz machine for $^1$H and 90.5 MHz for $^{13}$C, the chemical displacement δ are indicated in ppm with respect to the TMS as standard, the coupling constants J are expressed in Hz.

EXAMPLE 1

Synthesis of (1S,1'R)-2-[1-(3',3'-dimethyl-1'-cyclohexyl)ethoxy]-2-methylpropyl 2-propenoate To a suspension of NaH (0.368 mole) in 1000 ml of dry THF at 0° (ice-bath) were added dropwise 70.0 g of (1S,1'R)-2-[1-(3',3'-dimethyl-1'-cyclohexyl)ethoxy]-2-methyl-1-propanol (0.306 mole, [α]$^D_{20}$=+10.6° (1.7%, CHCl$_3$), diastereoisomeric purity ~80%, obtained according to the method described in EP 472966 and using a starting compound having a comparable enantiomeric and diastereoisomeric purity). After the end of the hydrogen evolution, 33.3 g (0.368 mole) of acryloyl chloride were added dropwise and the mixture thus obtained was stirred for 90 minutes at room temperature, and for 48 hours at reflux. After cooling at 0° and the addition of 350 ml of water, the reaction mixture was poured into 250 ml of 1M HCl, extracted twice with 600 ml of ether, washed once with saturated NaHCO$_3$, twice with brine, dried over Na$_2$SO$_4$ and concentrated under vacuum. A distillation on residue (Eb$_{(0.05}$mbar)=73–96°) furnished 81.35 g of 65% crude material which were purified by flash chromatography over SiO$_2$ (eluent:pentane/ether=96:4). The more pure fractions were mixed together, concentrated under vacuum and distilled (bulb to bulb, 0.06 mbar, oven=125°) to give 64.4 g (yield=74%) of a 96% pure 2-[1-(3',3'-dimethyl-1'-cyclohexyl)ethyoxy]-2-propenoate in the form of a mixture containing 81% of the (1S,1'R) diastereoisomer and 19% of three other diastereomers.

[α]$^D_{20}$=+5.6° (1.3%, CHCl$_3$)

$^1$H-NMR: 0.86 (s, 3H), 0.89 (s, 3H), 1.06 (d, J=6, 3H), 1.21 (s, 6H), 1.27–1.72 (m, 7H), 3.38 (q, J=6, 1H), 4.03 (s, 2H), 5.84 (d, J=10.3, 1H), 6.15 (dd, J$_1$=10.3, J$_2$=17.4, 1H), 6.43 (d, J=17.4, 1H).

$^{13}$C-NMR: 19.7 (q), 22.3 (t), 23.8 (q), 24.2 (q), 24.7 (q), 28.3 (t), 30.7 (s), 33.7 (q), 39.4 (t), 40.4 (d), 42.3 (t), 70.5 (t), 71.9 (d), 73.8 (s), 128.6 (d), 130.7 (t), 166.1 (s).

EXAMPLE 2

Synthesis of (1S,1'R)-2-[1-(3',3'-dimethyl-1'-cyclohexyl)ethoxy]-2-methylpropyl (E)-2-butenoate The title compound was prepared using the same procedure as described in Example 1 and using crotonyl chloride instead of acryloyl chloride. The desired product was obtained with a yield of 64%.

[α]$^D_{20}$=+7.1° (1.47%, CHCl$_3$)

$^1$H-NMR: 0.86 (s, 3H), 0.89 (s, 3H), 1.06 (d: J=6, 3H), 1.19 (s, 3H), 1.20 (s, 3H), 1.24–1.73 (m, 7H), 1.89 (dd, J$_1$=1.5, J$_2$=7, 3H), 3.37 (quint.: J=6, 1H), 3.99 (s, 2H), 5.87 (d: J=15.5, 1H), 6.99 (dq: J$_1$=7, J$_2$=15.5, 1H).

$^{13}$C-NMR: 18.0 (q), 19.7 (q), 22.3 (t), 23.8 (q), 24.3 (q), 24.7 (q), 28.3 (t), 30.7 (s), 33.7 (q), 39.4 (t), 40.4 (d), 42.3 (t), 70.1 (t), 71.8 (d), 73.8 (s), 122.8 (d), 144.7 (d), 166.4 (s).

EXAMPLE 3

Preparation of a Perfuming Composition

A perfuming composition of the "floral-musky" type for a powder detergent was prepared by admixing the following ingredients:

| Ingredient | Parts by weight |
| --- | --- |
| Hexylcinnamic aldehyde | 280 |
| 2-Methyldecanal | 20 |
| 9-Undecenal | 20 |
| Verdyl acetate | 80 |
| Coumarine | 20 |
| Allyl cyclohexylpropionate | 20 |
| 2-(4-Isopropylbenzyl)-2-methylpropanal | 20 |
| Dihydromyrcenol | 240 |
| Doremox ®[1)] | 10 |
| Iralia ®[2)] Total | 20 |
| Patchouli | 10 |
| Verdyl propionate | 80 |
| Amyl salicilate | 20 |
| Verdox ®[3)] | 60 |
| Yara Yara | 20 |
| 2,4-Dimethyl-3-cyclohexen-1-carbaldehyde | 10 |
| Lavandin Grosso | 10 |
| Total | 940 |

[1)]Tetrahydro-4-methyl-2-phenyl-2H-pyran; origin: Firmenich SA, Geneva, Switzerland
[2)]Mixture of methylionone isomers; origin: Firmenich SA, Geneva, Switzerland
[3)]2-Tert-butyl-1-cyclohexyl acetate; origin: International Flavors & Fragrances, USA The addition of 60 parts by weight of (1S,1'R)-2-[1-(3',3'-dimethyl-1'-cyclohexyl)ethoxy]-2-methylpropyl 2-propenoate to the above-described perfuming composition imparted to the latter a powerful musky aspect, which is also smooth and fresh, together with a green, pear's peel connotation and a Galbanum undernote.

EXAMPLE 4

Preparation of a Perfuming Composition

A perfuming composition of the "floral-musky" type for a softener was prepared by admixing the following ingredients:

| Ingredient | Parts by weight |
| --- | --- |
| Verdyl acetate | 50 |
| Cinnamic alcohol | 20 |
| Hexylcinnamic aldehyde | 250 |
| Benzophenone | 5 |
| Benzylacetone | 30 |
| Citronellol | 60 |
| Allyl cyclohexylpropionate | 5 |
| Dihydromyrcenol | 60 |
| Doremox ®[1)] | 5 |
| Iralia ®[2)] Total | 90 |
| 2,4,6-Trimethyl-4-phenyl-1,3-dioxane | 10 |
| Hedione ®[3)] | 30 |
| 10%* Indomethylene | 20 |
| 10%* Neobutenone ®[4)] | 20 |
| 10%* Trans-1-(2,2,6-trimethyl-1-cyclohexyl)-3-hexanol | 15 |
| Rose oxide | 30 |
| Phenylhexanol | 80 |
| Hexyl salicilate | 60 |

-continued

| Ingredient | Parts by weight |
| --- | --- |
| Vertofix Coeur ®[5] | 60 |
| Total | 900 |

*in dipropyleneglycol
[1])Tetrahydro-4-methyl-2-phenyl-2H-pyran; origin: Firmenich SA, Geneva, Switzerland
[2])Mixture of methylionone isomers; origin: Firmenich SA, Geneva, Switzerland
[3])Methyl dihydrojasmonate; origin: Firmenich SA, Geneva, Switzerland
[4])1-(5,5-Dimethyl-1-cyclohexen-1-yl)-4-penten-1-one; origin: Firmenich SA, Geneva, Switzerland
[5])Origin: International Flavors & Fragrances, USA The addition of 100 parts by weight of (1S,1'R)-2-[1-(3',3'-dimethyl-1'-cyclohexyl)ethoxy]2-methylpropyl 2-propenoate to the above-described composition imparted to the latter a powerful musky aspect, which is well perceivable on the bottle as well as on the linen. Moreover, the presence of the invention's compound, in the above-mentioned composition, exalted the fresh green character which was originally imparted by the Neobutenone® and Doremox®.

EXAMPLE 5

Preparation of a Perfuming Composition

A woman's eau de toilette of the "ozonic-floral" type for a softener was prepared by admixing the following ingredients:

| Ingredient | Parts by weight |
| --- | --- |
| 1%* Phenylacetic aldehyde | 20 |
| Beta Ionone | 50 |
| Citronellol | 50 |
| γ-n-Decalactone | 5 |
| Eugenol | 10 |
| Hedione ® HC[1]) | 150 |
| 3-(1,3-Benzodioxol-5-yl)-2-methylpropanal | 50 |
| 10%* Indol | 15 |
| Iso E super ®[2]) | 200 |
| Lilial ®[3]) | 150 |
| Linalool | 100 |
| Myroxyde ®[4]) | 40 |
| 10%* Neobutenone ®[5]) | 20 |
| 10%* 2,6-Dimethyl-5-heptanal | 20 |
| 7-Tert-butyl-2H,4H-1,5-benzodioxepin-3-one | 10 |
| Feuillage vert base 47062[6]) | 10 |
| Total | 900 |

*in dipropyleneglycol
[1])Methyl dihydrojasmonate; origin: Firmenich SA, Geneva, Switzerland
[2])1-(Octahydro-2,3,8,8-tetramethyl-2-naphtalenyl)-1-ethanone; origin: International Flavors & Fragrances, USA
[3])3-(4-Tert-butylphenyl)-2-methylpropanal; origin: Givaudan-Roure SA, Vernier, Switzerland
[4])6,7-Epoxy-3,7-dimethyl-1,3-octadiene; origin: Firmenich SA, Geneva, Switzerland
[5])1-(5,5-Dimethyl-1-cyclohexen-1-yl)-4-penten-1-one; origin: Firmenich SA, Geneva, Switzerland
[6])Compounded perfumery base; origin: Firmenich SA, Geneva, Switzerland The addition of 100 parts by weight of (1S,1'R)-2-[1-(3',3'-dimethyl-1'-cyclohexyl)ethoxy]-2-methylpropyl 2-propenoate to the above-described eau de toilette imparted to the latter a transparent, crystalline and fresh musky character. The eau de toilette thus obtained acquired more volume and impact, and become more natural and fine perfumery. The addition of the invention's compound also rounded the Galbanum note, provided by the Neobutenone®, by providing to the latter a sparkling and "mouth-watering" acpect of the powdery-fruity-pear's peel type.

The invention claimed is:

1. A perfuming composition comprising:
   i) as perfuming ingredient, at least a compound of formula

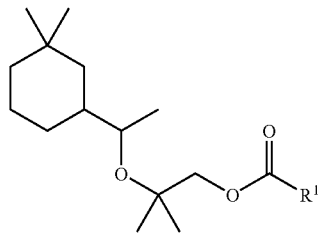

(I)

in the form of anyone of its isomers or a mixture thereof, and in which $R^1$ represents a linear or branched $C_2$ to $C_4$ alkenyl group;

ii) at least one ingredient selected from the group consisting of a perfumery carrier and a perfumery base; and iii) optionally at least one perfumery adjuvant.

2. A perfuming composition according to claim 1, characterized in that the perfuming ingredient is a compound of formula

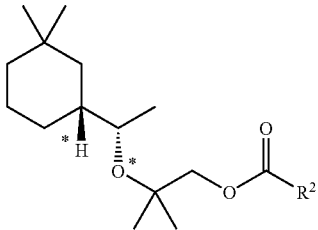

(II)

in the form of any of its isomers or a mixture thereof, and in which $R^2$ represents a linear or branched $C_2$ or $C_3$ 1-alkenyl group, and the hydrogen and oxygen atom marked with an asterisk are in a trans configuration.

3. A perfuming composition according to claim 1, characterized in that the perfuming ingredient is (1S, 1'R)-2-[1-(3',3'-dimethyl-1'-cyclohexyl)ethoxy]-2-methylpropyl 2-propenoate.

4. A perfumed article comprising:
   i) a perfuming composition as defined in any one of claims 1 to 3; and
   ii) a consumer product base.

5. A perfumed article according to claim 4, characterized in that the consumer product base is a solid or liquid detergent, a fabric softener, a perfume, a cologne or aftershave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

6. A method to confer, enhance, improve or modify the odor properties of a perfuming composition or of a perfumed article, which method comprise adding to said composition or article an effective amount of a perfuming composition as defined in any one of claims 1 to 3.

7. A compound of formula (I)

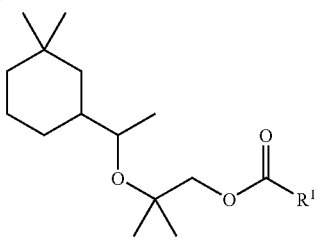

in the form of any of its isomers or a mixture thereof, and in which $R^1$ represents a linear or branched $C_2$ to $C_4$ alkenyl group; provided that 2-[1-(3,3-dimethylcyclohexyl)ethoxy]-2-methylpropyl 2-methyl-2-butenoate is excluded.

8. As a compound according to claim 7, of formula (II)

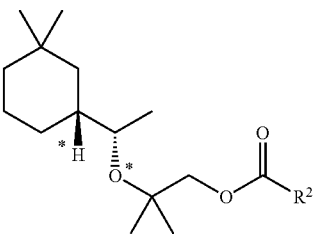

in the form of any of its isomers or a mixture thereof, and in which $R^2$ represents a linear, branched $C_2$ or $C_3$ 1-alkenyl group, and the hydrogen and oxygen atom marked with an asterisk are in a trans configuration.

9. As a compound according to claim 7, (1S,1'R)-2-[1-(3',3'-dimethyl-1'-cyclohexyl)ethoxy]-2-methylpropyl 2-propenoate.

10. A perfumed article comprising:
  i) as perfuming ingredient, at least a compound of formula (I) as defined in any one of claims 1 to 3; and
  ii) a consumer product base.

11. A perfumed article according to claim 10, characterized in that the consumer product base is a solid or liquid detergent, a fabric softener, a perfume, a cologne or aftershave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

12. A method to confer, enhance, improve or modify the odor properties of a perfuming composition or of a perfumed article, which method comprise adding to said composition or article an effective amount of a compound as defined in any one of claims 1 to 3.

* * * * *